United States Patent [19]

Hirsch et al.

[11] 4,405,801

[45] Sep. 20, 1983

[54] SILICON-CONTAINING NITRO DYES AND PROCESS FOR MAKING THE SAME

[75] Inventors: Bodo Hirsch, Graupa; Gunter Horn, Nuenchritz; Hellmut Reuther, Dresden, all of German Democratic Rep.

[73] Assignee: VEB Chemiewerk Nünchritz, Radebeul, German Democratic Rep.

[21] Appl. No.: 391,657

[22] Filed: Jun. 24, 1982

Related U.S. Application Data

[63] Continuation of Ser. No. 27,266, Apr. 5, 1979, abandoned.

[30] Foreign Application Priority Data

Apr. 5, 1978 [DD] German Democratic Rep. ... 204588

[51] Int. Cl.³ .................................................. C07F 7/10
[52] U.S. Cl. ........................................ 556/422; 8/404; 8/649
[58] Field of Search .......................................... 556/422

[56] References Cited

U.S. PATENT DOCUMENTS

| 2,756,246 | 7/1956 | Burkhard | 556/422 |
| 2,985,680 | 5/1961 | Pepe | 556/422 |
| 3,375,218 | 3/1968 | Bailey et al. | 556/422 X |
| 3,731,205 | 4/1964 | Frankel | 556/422 |
| 4,139,403 | 2/1979 | Baum et al. | 556/422 X |

*Primary Examiner*—Paul F. Shaver
*Attorney, Agent, or Firm*—Gabriel P. Katona

[57] ABSTRACT

Disclosed are silicon-containing nitro dyes for dying organic polymers or organosiloxanes, which are reactive dyes for synthetic or natural fibers of vegetable or animal origin, having the formula:

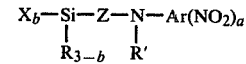

wherein the chromophore component is bonded with the Si-atom by homopolar bonds and wherein X represents the same or different hydrolyzable groups or a siloxane radical, Z is a bivalent alkylene radical with 1-10 carbon atoms which may be interrupted by NR' groups, R is a monovalent organic radical, R' is hydrogen, alkyl with 1-10 carbon atoms, aryl, aralkyl or said substituted radicals, Ar is a substituted or unsubstituted aryl radical, and a and b are integers from 1-3, and a process for making said dyes. Said dyes may be built into a large number of organic and inorganic molecules and color the same without fixation.

3 Claims, No Drawings

SILICON-CONTAINING NITRO DYES AND PROCESS FOR MAKING THE SAME

CROSS-REFERENCE TO RELATED APPLICATION

This application is a continuation of application Ser. No. 27,266, filed Apr. 5, 1979, now abondoned.

SUMMARY OF THE INVENTION

The present invention relates to silicon-containing nitro dyes for dyeing organic polymers, especially for coloring silicone products as well as inorganic materials, the dyes being reactive dyes for synthetic or natural fibers of vegetable or animal origin. The dyes may be built into the polymer molecule or applied to the fibers without additional fixation, respectively.

BACKGROUND AND PRIOR ART

It is already known to produce and use dyes for dyeing silicones and other polymers which are built up from an organic amino-silicon compound. These latter compounds are used because they are easily accessible and are capable of many varieties of reaction. Thus it was already proposed to make azo dyes by reaction of aminoarylalkylsilanes with suitable intermediate dyes. For instance, for dyeing glass fibers, the hydroxyl groups in the glass surface were reacted with the silane solution capable of coupling, and subsequently treated with a diazotized solution (U.S. Pat. No. 2,934,459). It is moreover possible to produce silicon-containing azo dyes by diazotation of aminoarylalkylsilanes and subsequent coupling with aromatic compounds (U.S. Pat. No. 2,927,839).

Triazin dyes are further known made by reaction of aminoalkylalkoxysilanes with aminoazo dyes and cyanur chloride (U.S. Pat. No. 2,963,338). Also thiazine dyes made by oxidation of a mixture of arylaminoalkylsilane p-diaminoazobenzene and thiosulfate (U.S. Pat. No. 2,955,898) as well as triarylmethane dyes from arylaminoalkylsilane with arylaldehyde or arylketone (U.S. Pat. No. 2,955,899). Hemzawi and Jones, J. Soc. Dyers and Colorists 85(9), 40 (1969) presented anthraquinone dyes which contain the aminoalkylsilyl group.

From U.S. Pat. Nos. 3,888,891, 3,963,744 and 3,981,859 dyes have become known which are especially compatible with silicones if they contain as silicon component a tris-(trimethylsiloxy-)silylalkylamino radical. These are mainly quinone-, indigo-, thioindigo-, phthalocyanine- and azo dyes.

However, the preparation of the mentioned silicon-containing dyes is very expensive because complicated operations have to be carried out. In these, the functional silicon groups contained in the starting components are removed which are responsible for the good compatibility with other materials so that these groups are no longer effective as reactive groups. It follows that a lasting coloring of e.g. silicone resins, silicone rubbers, and other silicone products based on syneresis phenomena during hardening or cross-linking will be prevented from occurring with these dyes. The tris-(trimethylsiloxy-)silyl group is no longer capable of reacting with suitable functional groups in the polymers so that the dyes remain in the polymers only by physical force but without chemical anchoring.

OBJECT OF THE INVENTION

It is the object of the present invention to produce so far unknown dyes from easily available starting materials in a simple and inexpensive manner, and in good yields. The chromophore components are to be built into the polymer structures, if possible, by homopolar bonds.

Furthermore, the stability and lasting coloring property of the novel dyes should come up to the high and particular specifications of silicone technology and they should be capable of dyeing polymer materials, especially silicone products, for lasting effects.

DETAILED DESCRIPTION OF THE INVENTION

It has been found that silicon-containing nitro dyes according to the invention will fulfill the objects above indicated. The dyes have the general formula

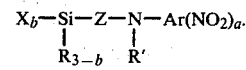

Of the high qualifications mentioned above, expected from the products according to the invention, we mention, by way of example, temperature stability.

In the general formula:
X represents equal or different hydrolyzable groups or a siloxane radical
Z is a bivalent alkylene radical with 1 to 10 C-atoms which may be interrupted by NR' groups
R respectively a monovalent organic radical
R' respectively hydrogen, alkyl with 1 to 10 C-atoms, aryl, aralkyl or such substituted radicals
Ar respectively a substituted or unsubstituted aryl radical a and b are integers from 1 to 3

The production of the novel silicon-containing dyes according to the invention is very simple and can be brought about by reacting silanes or siloxanes of the general formula

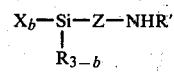

with nitro compounds of the general formula

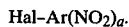

In the formulas, the symbols X, Z, R, R', a and b have the same meanings as explained before; Hal stands for halogen.

An -NHR'-group reacts with the halogen of the nitroaryl compound by splitting off HCl. In most cases, simple mixing of the starting material at normal temperature is sufficient, with the mostly crystalline nitro compound becoming dissolved in the silane under evolution of heat. By slightly heating, the reaction can be enhanced. The reaction takes place stoichiometrically, that is to say, one amino group reacts with one nitroaryl molecule.

As halogennitroaryl compounds we also may use further substituted compounds, e.g. -SO$_3$H-containing compounds. Other possible substituents are -ROH, -RON, -RCONH$_2$, -RCOOR and others.

The reaction can also be carried out in solvents, water, and organic solvents e.g. alkanols, toluene, or dimethylformamide being suitable. The reaction of nitroaryl compounds with partly condensed polyorganosiloxanes can also be effected in solvents if siloxy groups with -Z-NHR' radicals were included in the condensation. These products are suitable as toning pastes for coloring silicon products.

The nitro dyes of this invention are particularly useful for dyeing organopolysiloxanes. The concentration of dyestuff in the siliconpolymers may be from 0.1 to 5% calculated as mass and is preferably chosen between 0.2 and 2%. The dyes according to the invention have the advantage that the coloring component is built into the polymer molecule by homopolar bonds. In principle, the dye itself can be polymerized to form a silicone oil, silicone rubber, or silicone resin, due to hydrolyzable and therefore condensable groups remaining at the silicon atom. The type of the final product depends on the functionality of the starting material. Since the functional groups remain at the silicon atom, all modifications known of the silanes (e.g. of silicic acids) can be dyed with the dyes according to the invention.

The nitro dyes according to the invention, wherein the dye is built into the silicon molecule by means of a homopolar bond, are thermo-stable; merely during extremely long exposure to temperature around 200° C., a light discoloration from yellow to brownish hues can occur. To the organopolysiloxanes dyed with the dyes of the invention, the conventional additives (fillers, reinforcing agents, e.g. calcium carbonate, zinc oxide, clay, quarz powder, glass- or metal fibers, amorphous silica, etc.) can be added, without causing difficulties and without impairing the dye.

The nitro dyes according to the invention are, as mentioned, reactive dyes, suitable for dyeing natural and synthetic fibers, such as wool, silk, cotton, regenerated fibers, polyamides, polyester and so on. They are also suitable for dyeing inorganic materials, e.g. highly dispersed silicid acid, glass fibers, etc. It is advantageous to carry out the dyeing of these materials in a dye solution, namely the dye dissolved in water, alcohol, or aromatics by simple steeping, with subsequent rinsing and washing. A further fixation is not necessary since the reactive groups present in the dye enter into a homopolar bond with the substrate.

EXAMPLES

The invention will now be more fully described in a number of examples which are given by way of illustration and not of limitation; all parts given are by way of mass.

EXAMPLE 1

20.3 parts 2,4-dinitrochlorobenzene are mixed in a beaker by gentle shaking with 23 parts of aminopropyltriethoxysilane. The mixture heats up rapidly and the 2,4-dinitrochlorobenzene dissolves in the silane with gas evolution. After cooling to room temperature, a yellow, liquid dye is obtained having the following formula:

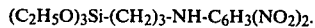

(C$_2$H$_5$O)$_3$Si-(CH$_2$)$_3$-NH-C$_6$H$_3$(NO$_2$)$_2$.

Two parts of the dye are added to a silicon-rubber paste consisting of 100 parts of a polydimethylsiloxane having hydroxyl groups and a viscosity of 5000 cSt, 50 parts of amorphous SiO$_2$ and one part of water. By addition of 3 parts of a mixture of dibutyltindilaurate and tetraoxysilane the rubber paste was cross-linked. The result was an intensely colored yellow silicone rubber. This rubber was heated for 24 hours to a temperature of 180° C., which did not cause any discoloration of the rubber.

When the silicone-rubber paste is only partly condensed with the dye without addition of a cross-linking agent, the product can be used as toning paste for silicone-rubber mixtures.

EXAMPLE 2

20.3 part of 2,4-dinitrochlorobenzene are dissolved at elevated temperature in a round flask in ethanol. 26.6 parts of aminoethylaminopropyltrimethoxysilane are added to the solution, which immediately becomes intensely yellow. Afer distilling off the ethanol, a dark yellow liquid remains.

5 g of the dye are dissolved in 95 g water and into the solution 5 g cotton, 5 g wool, 5 g polyamide fiber, 5 g polyacrylnitrile fiber, 5 g polyester silk, and 5 g cellulose fiber are steeped for 5 minutes each.

After rinsing and repeated washing in soap solution the fibers retain the yellow coloring obtained by the dye.

EXAMPLE 3

20.3 parts of 2,4-dinitrochlorobenzene are dissolved in a brown flask in ethanol at elevated temperature. 10.4 parts of aminoethylaminopropyl-(methyl)-dimethoxysilane are added to the solution, which turns to a deep yellow liquid. 100 parts of a transparent methylphenylsilicone resin are stirred with 0.2 parts of the thus obtained dye and subsequently hardened at a temperature of 200° C. for 2 hours. Obtained is a solid, yellow, transparent silicone resin. If the dye components are only partly condensed with the silicon-resin components, namely not hardened, this product can be used as a toning paste for silicone resins.

EXAMPLE 4

To 82 parts of a polymethylsiloxane, which has a molecular weight of 820 and contains an amino group in the molecule, 20.2 parts of dinitrochlorobenzene are added in small portions, during which procedure the silicone liquid turns yellow with evolution of heat.

A mixture is then produced of 500 g of a hydroxyl group-end-blocked polymethylsiloxane having a viscosity of about 5000 cSt and 0.05 g of the yellow silicone liquid, and thereto are added 3 g of a cross-linking agent made by mixing 80 parts of tetraethoxysilane and 20 parts of dibutyltindilaurate, and the whole mass is stirred. After about 24 hours storage at room temperature, a transparent yellow silicone rubber is obtained.

We claim:

1. Silicon-containing nitro dyes having the formula:

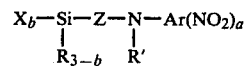

wherein the coloring component is bonded with the Si-atom by homopolar bonds and wherein X represents same or different hydrolyzable groups or a siloxane radical, Z is a bivalent alkylene radical with 1–10 carbon atoms which may be interrupted by NR' groups, R is a monovalent organic radical, R' is hydrogen, alkyl with 1–10 C-atoms, aryl, aralkyl or said substituted radicals, Ar is a substituted or unsubstituted aryl radical, and a and b are integers from 1–3.

2. A process for making silicon-containing nitro dyes having the formula:

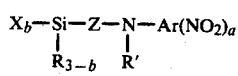

comprising the step of coupling silanes or siloxanes of the formula:

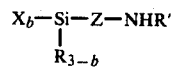

with nitroaryl compounds of the formula:

Hal-AR(NO$_2$)$_a$ wherein X represents same or different hydrolyzable groups or a siloxane radical, Z is a bivalent alkylene radical with 1–10 C-atoms which may be interrupted by NR' groups, R is a monovalent organic radical, R' is hydrogen, alkyl with 1–10 C-atoms, aryl, aralkyl or said substituted radicals, Ar is a substituted or unsubstituted aryl radical, a and b are integers from 1–3, and Hal represents halogen, the reaction being carried out at normal or slightly elevated temperatures in stoichiometric ratio.

3. The process of claim 2, wherein the coupling reaction is carried out in a solvent.

* * * * *